United States Patent [19]

Chang

[11] Patent Number: 5,229,503
[45] Date of Patent: Jul. 20, 1993

[54] LYSINE-N-AMINO REACTIVE AND CYSTEINE-MERCAPTO REACTIVE AZO DYES

[75] Inventor: Jui Y. Chang, Bubendorf, Switzerland

[73] Assignee: Ciba-Geigy Corporation, Ardsley, N.Y.

[21] Appl. No.: 758,249

[22] Filed: Sep. 11, 1991

Related U.S. Application Data

[63] Continuation of Ser. No. 348,315, May 5, 1989, abandoned.

[30] Foreign Application Priority Data

May 10, 1988 [CH]  Switzerland ............... 1766/88
Mar. 22, 1989 [CH]  Switzerland ............... 1065/89

[51] Int. Cl.$^5$ .................. C09B 29/085; G01N 33/68
[52] U.S. Cl. .................. 534/735; 534/591; 534/593; 534/728; 534/845; 534/851; 534/887; 436/86; 436/90
[58] Field of Search .................. 534/735, 799

[56] References Cited

U.S. PATENT DOCUMENTS

| | | | |
|---|---|---|---|
| 1,916,314 | 7/1933 | Hilger | 534/735 |
| 2,022,935 | 12/1935 | Hilger et al. | 534/735 X |
| 2,042,600 | 6/1936 | Hilger et al. | 534/735 X |
| 3,051,542 | 8/1962 | Bosshard et al. | 534/735 X |
| 3,966,900 | 6/1976 | Hennart et al. | 514/136 |

FOREIGN PATENT DOCUMENTS

| | | |
|---|---|---|
| 456234 | 2/1928 | Fed. Rep. of Germany . |
| 1932690 | 6/1969 | Fed. Rep. of Germany . |
| 2362859 | 6/1975 | Fed. Rep. of Germany . |
| 2622517 | 12/1977 | Fed. Rep. of Germany . |

OTHER PUBLICATIONS

Sun et al, Journal of Biological Chemistry, 264(19) 11288-11293 (Jul. 5, 1989).
Chang II, Mod. Methods Protein Chem., 2, 275-85 (1985).
Sigrist et al, J. Mol. Biol., 173(1), 93-108 (1984).
Harris et al. J. Am. Chem. Soc. 52, 2397 (1930).
Liu et al, Analytical Biochemistry 127, 426 (1982).
Chang I. J. Biol. Chem. 7141 (1989).

(List continued on next page.)

*Primary Examiner*—David B. Springer
*Assistant Examiner*—Fiona T. Powers
*Attorney, Agent, or Firm*—Irving M. Fishman; Karen G. Kaiser; Barbara J. Ikeler

[57] ABSTRACT

The invention relates to azo compounds, especially to compounds of formula

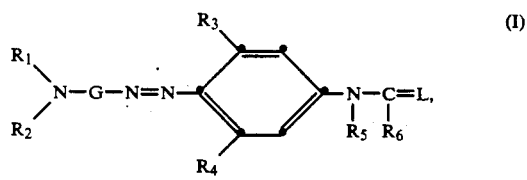

wherein $R_1$ is lower alkyl, $R_2$ is lower alkyl, $R_3$ is hydrogen, carboxy or sulfo, $R_4$ is carboxy or sulfo, G is an unsubstituted or substituted 1,4-phenylene group or an unsubstituted or substituted 1,4-naphthylene group, and wherein either $R_5$ and $R_6$ together are an additional bond and L is an oxygen or sulfur atom or wherein $R_5$ is hydrogen, $R_6$ is halomethyl and L is an oxygen atom, and salts thereof, to the use of compounds I and their salts, to a process for the preparation of compounds I and their salts, to starting materials used in that preparation process, and salts thereof, to a process for the preparation of those starting materials and their salts, to a device in which the compounds I and their salts are used, and to a process in which that device is used. The compounds of formula I can be used as adjuncts in the investigation of proteins and can be prepared in a manner known per se.

4 Claims, 1 Drawing Sheet

OTHER PUBLICATIONS

Antos, K., *Chemical Abstracts,* vol. 54, No. 22432c (1960).

Baldwin, R. W. et al, *Chemical Abstracts,* vol. 54, No. 25212b (1960).

Chang, J., *Chemical Abstracts,* vol. 104, No. 84699m (1986).

Chang, J., *J. Biol. Chem.,* 264(6), 3111-15 (1989).

Chang et al, *J. Chromatogr.* 132(2), 303-7 (1977).

Sun et al, *Chemical Abstracts,* vol. 111, No. 129570a (1989).

Yu et al, *Chemical Abstracts,* vol. 95, No. 203600e (1981).

Yem et al., J. of Biological Chemistry 264, No. 30, 17691-17697, Oct. 25, 1989 Biotinylation of Reactive Amino Groups in Native Recombinant Human Interleukin-1B.

Eisenberg et al, Nature 343, 341-346, Jan. 25, 1990, Primary Structure and Functional Expression from Complementary DNA of a Human Interleukin-1 Receptor Antagonist.

Sun et al, Eur. J. Biochem. 185, 225-230 (Oct. 11, 1989), The Heparin and Pentosan Polysulfate Bonding Sites of Human Antithrombin Overlap but are not Identical.

Chang, J. of Biological Chemistry 264, No. 13, 7141-7146 (May 5, 1989), the Hirudin Binding Site of Human α-thrombin.

Chang et al, Biochemistry 31, 2874-2878 (1992), Identification of a Reactive Lysyl Residue (Lys[103]) of Recombinant Human Interleukin-1B.

Chang, Biochemistry, 30, No. 27, 6656-6661 (1991), Deciphering the Structural Elements of Hirudin C-Terminal Peptide that Bind to the Fibrinogen Recognition Site of α-Thrombin.

Priestle et al, Proc. Natl. Acad. Sci. USA, 86: 9667-9671 (Dec. 1989), Crystallographic Refinement of Interleukin 1B at 2.0Å Resolution.

Lee et al, J. Mol. Biol. 55, 379-400 (1971), The Interpretation of Protein Stuctures: Estimation of Static Accessibility.

Lowenthal et al, J. Exp. Med. 164, 1060-1074 (Oct. 1986), Binding and Internalization of Intereleukin 1 by T Cells.

Joss et al, J. Receptor Research, 11(1-4), 275-282 (1991), Mapping the Receptor Binding Domain of Interleukin-1 Beta by Means of Binding Studies Using Overlapping Sequence Fragments.

Chang, Biochem. J. 163, 517-520 (1977), High-Sensitivity Sequence Analysis of Peptides and Proteins by 4-N,N-Dimethylaminoazobenzene 4'-Isothiocyanate.

Chang et al, Biochem. J. 153, 607-611 (1976), 4-N,-N-Dimethylaminoazobenzene 4'-Isothiocyanate, a New Chromophoric Reagent for Protein Sequence Analysis, Lubert Stryer, "Biochemistry" 3rd Ed. W. H. Freeman & Co., New York (1988) p. 21.

FIG. 1

LYSINE-N-AMINO REACTIVE AND CYSTEINE-MERCAPTO REACTIVE AZO DYES

This application is a continuation of application Ser. No. 348,315, filed May 5, 1989, now abandoned.

The invention relates to novel aromatic acids, especially compounds of formula wherein $R_1$ is lower alkyl, $R_2$ is lower alkyl, $R_3$ is hydrogen, carboxy or sulfo, $R_4$ is carboxy or sulfo, G is an unsubstituted or substituted 1,4-phenylene group or an unsubstituted or substituted 1,4-naphthylene group, and wherein either $R_5$ and $R_6$ together are an additional bond and L is an oxygen or sulfur atom or wherein $R_5$ is hydrogen, $R_6$ is halomethyl and L is an oxygen atom, and salts thereof, to the use of compounds I and their salts, to a process for the preparation of compounds I and their salts, to starting materials used in that preparation process, and salts thereof, to a process for the preparation of those starting materials and their salts, to a device in which the compounds I and their salts are used, and to a process in which that device is used.

Suitable unsubstituted or substituted 1,4-phenylene groups are, for example, unsubstituted or carboxy- and-/or sulfo-substituted 1,4-phenylene groups, the substituted 1,4-phenylene groups having from 1 up to and including 4, especially 1 or 2, of the mentioned substituents. If the substituted 1,4-phenylene groups contain more than one substituent, then some or all of those substituents may be identical. Examples that may be mentioned are the 2-sulfo-, 2,3-, 2,5- and 3,5-disulfo-, 2,3,5-trisulfo-and 2,3,5,6-tetrasulfo-1,4-phenylene group, the 2-carboxy-, 2,3-, 2,5- and 3,5-dicarboxy-, 2,3,5-tricarboxy- and 2,3,5,6-tetracarboxy-1,4-phenylene group, the 2-carboxy-3-sulfo-, 2-carboxy-5-sulfo-, 3-carboxy-5-sulfo-, 2,3-dicarboxy-5-sulfo-, 3,5-dicarboxy-2-sulfo-, 5-carboxy-2,3-disulfo-and 2-carboxy-3,5-disulfo-1,4-phenylene group and especially the 1,4-phenylene group.

Suitable unsubstituted or substituted 1,4-naphthylene groups are, for example, unsubstituted or carboxy- and-/or sulfo-substituted 1,4-naphthylene groups, the substituted 1,4-naphthylene groups containing from 1 up to and including 6, especially from 1 up to and including 3, of the mentioned substituents. If the substituted 1,4-naphthylene groups contain more than one substituent, then some or all of those substituents may be identical. Examples that may be mentioned are the 2-, 5- and 6-sulfo-, 2,3-, 5,6-, 6,7- and 2,6-disulfo-, 2,3,5- and 2,3,6-trisulfo- and 2,3,5,7-and 2,3,6,7-tetrasulfo-1,4-naphthylene group, the 2-, 5- and 6-carboxy-, 2,3-, 5,6-, 6,7- and 2,6-dicarboxy-, 2,3,5- and 2,3,6-tricarboxy- and 2,3,5,7- and 2,3,6,7-tetracarboxy-1,4-naphthylene group, the 2-carboxy-3-sulfo-, 2-carboxy-5-sulfo-, 3-carboxy-6-sulfo-, 5-carboxy-7-sulfo-, 2,3-dicarboxy-5-sulfo-, 3,5-dicarboxy-2-sulfo-, 6,7-dicarboxy-2-sulfo-, 3-carboxy-6,7-disulfo-, 5-carboxy-2,3-disulfo- and 2-carboxy-3,5-disulfo-1,4-naphthylene group and especially the 1,4-naphthylene group.

The invention relates, for example, to compounds I wherein $R_1$ is lower alkyl, $R_2$ is lower alkyl, $R_3$ is hydrogen, carboxy or sulfo, $R_4$ is carboxy or sulfo, G is an unsubstituted or substituted 1,4-phenylene group or an unsubstituted or substituted 1,4-naphthylene group, $R_5$ and $R_6$ together are an additional bond and L is an oxygen or sulfur atom, and salts thereof.

Some of the compounds I can be in the form of stereoisomers. For example, if the compounds I contain at least one chiral carbon atom (C atom) (for example a C atom of a corresponding radical $R_1$), they can be, for example, in the form of pure enantiomers or mixtures of enantiomers, such as racemates, and if there is at least one further chiral centre present (for example a C atom of a corresponding radical $R_2$), they may also be in the form of diastereoisomers, mixtures of diastereoisomers or mixtures of racemates.

Salts of compounds I are especially salts with bases, preferably pharmaceutically acceptable salts with bases, for example alkali metal salts or alkaline earth metal salts, for example sodium, potassium or magnesium salts, transition metal salts, such as zinc or copper salts, or salts with ammonia or organic amines, such as cyclic amines, such as mono-, di-or tri-lower alkylamines, such as hydroxy-lower alkylamines, for example mono-, di- or tri-hydroxy-lower alkylamines, hydroxy-lower alkyl-lower alkylamines or polyhydroxy-lower alkylamines. Cyclic amines are, for example, morpholine, thiomorpholine, piperidine or pyrrolidine. Suitable mono-lower alkylamines are, for example, ethylamine or tert.-butylamine; suitable di-lower alkylamines are, for example, diethylamine or diisopropyl-amine; and suitable tri-lower alkylamines are, for example, trimethylamine or triethylamine. Suitable hydroxy-lower alkylamines are, for example, mono-, di- or tri-ethanolamine, and hydroxy-lower alkyl-lower alkylamines are, for example, N,N-dimethylamino- or N,N-diethylaminoethanol, whilst a suitable polyhydroxy-lower alkylamine is, for example, glucosamine. The compounds I can also form acid addition salts, preferably pharmaceutically acceptable acid addition salts, for example with strong inorganic acids, such as mineral acids, for example sulfuric acid, a phosphoric acid or a hydrohalic acid, with strong organic carboxylic acids, such as lower alkanecarboxylic acids, for example acetic acid, saturated or unsaturated dicarboxylic acids, for example malonic, maleic or fumaric acid, or hydroxycarboxylic acids, for example tartaric or citric acid, or with sulfonic acids, such as lower alkanesulfonic acids or unsubstituted or substituted benzenesulfonic acids, for example methane- or p-toluene-sulfonic acid. The compounds I can also form inner salts.

Also included are salts of compounds I that are less suitable for pharmaceutical uses. These may be used, for example, for the isolation or purification of free compounds I according to the invention and their pharmaceutically acceptable salts.

Hereinbefore and hereinafter, unless defined otherwise, radicals or compounds designated "lower" are to be understood as being especially those radicals or compounds containing up to and including 7, especially up to and including 4, carbon atoms.

Lower alkyl is, for example, $C_1$–$C_4$alkyl, such as methyl, ethyl, n-propyl, isopropyl, n-butyl, isobutyl, sec.-butyl or tert.-butyl, and also includes $C_5$–$C_7$alkyl radicals, that is to say pentyl, hexyl and heptyl radicals.

Halomethyl is fluoro-, chloro- or bromo-methyl, but especially iodo-methyl.

The compounds I and their salts have valuable properties. For example, they can be used as adjuncts in the investigation of proteins, for example as reagents for the chemical modification of proteins. Hereinbefore and hereinafter the term "protein" is to be understood as including both peptides having a relative molecular weight of 10 000 or more atomic mass units, which are generally termed proteins, and peptides having a relative molecular weight of less than 10 000 atomic mass units, which are generally termed polypeptides, a lower limit of from approximately 1000 to approximately 2000 atomic mass units applying to the relative molecular weight of the polypeptides. Examples taken from the numerous applications in which the chemical modification of proteins can play a part are the structural analysis and the coloration of proteins.

It is known that the modification of a single amino acid building block or of a small number thereof can substantially alter the spatial structure of a protein and therefore also its function, for example its biological activity. This opens up the possibility of using the specific chemical modification of amino acid building blocks as a widely applicable method of determining the contribution made by these building blocks to the spatial structure of a protein. The problem arises here of relating any alteration in the spatial protein structure occurring as a result of a certain chemical modification of amino acid building blocks to the nature and extent of that chemical modification. For this purpose the structure of a corresponding chemically modified protein must be determined and compared with the structure present before the chemical modification was carried out. One of the aims of this kind of structural analysis is to determine in what way the protein primary structure has changed during the chemical modification, that is to say which amino acid building blocks have been chemically modified. In primary structure analyses of this kind, the procedure is often as follows: a chemically modified protein $M_a$, obtained after chemical modification of a corresponding unmodified protein $N_a$, and the unmodified protein $N_a$ are, optionally after having carried out a denaturation step which may be necessary, each treated with the same protease, the two peptide mixtures $M_a{}^1$ and $N_a{}^1$ so obtained are each subjected to high-performance liquid chromatography (HPLC) and the peak patterns in the two resulting chromatograms $M_a{}^2$ and $N_a{}^2$ are compared with one another. The detection systems used for recording these chromatograms are usually detection systems which evaluate the light absorption behaviour of the peptides. The peak pattern in chromatogram $M_a{}^2$ generally differs from the peak pattern in chromatogram $M_a{}^2$ at those places at which peptides $M_a{}^3$, which contain at least one chemically modified amino acid building block, are detected, since the peptides $M_a{}^3$ generally exhibit a light absorption behaviour different from that of the corresponding unmodified peptides $N_a{}^3$. The peptides $M_a{}^3$ are separated off and subjected to further primary structure analysis, for example to amino acid sequence analysis. Ideally, each chemically modified amino acid building block can be identified and characterised in this manner.

In many cases, however, the usefulness of the above-described procedure leaves something to be desired. For example, when the protein to be investigated has a relatively high relative molecular weight, there are normally so many different peptides present in the corresponding peptide mixture after the protease treatment that HPLC is unable to effect sufficient separation of the peptide mixture. Furthermore, the chemical modification itself is often too complex; it often proceeds in a non-specific manner and therefore affects a large number of structurally different amino acid building blocks or even all the amino acid building blocks in the protein under investigation; advantageously, however, it should be possible to carry out the chemical modification as specifically as possible, that is to say specifically directed only at a class of amino acid building blocks that is defined as accurately as possible and advantageously that is narrowly defined in terms of nature and number.

It is therefore desirable and of great practical interest to optimise the procedure described above by overcoming the disadvantages indicated. The compounds I disclosed within the framework of the present invention and their salts make such an optimisation possible. This optimisation is explained in detail below with reference to compounds I in which $R_1$, $R_2$, $R_3$, $R_4$ and G are as defined above, $R_5$ and $R_6$ together are an additional bond and L is an oxygen or sulfur atom, and salts thereof. These compounds are designated compounds IA below.

In the chemical modification of a protein, that is to say in the reaction with that protein, the compounds IA and their salts react in the first instance virtually exclusively with the amino groups in the ε-position of lysine building blocks, with high reactivity being observed. Only in isolated cases is there additionally a reaction with the amino group of the N-terminal amino acid building block of the protein in question. The nature and number of the amino acid building blocks of a protein that are affected by a chemical modification by a compound IA or a salt thereof are therefore clear and, advantageously, narrowly defined. Thus the number of chemically modified amino acid building blocks is generally not greater than the number of lysine building blocks in the protein under investigation. Only in isolated cases, when there is an additional N-terminal modification, can it be greater by 1.

Furthermore, the use of a compound IA or a salt thereof for the chemical modification of a protein has the great advantage that after the protease treatment of the resulting chemically modified protein $M_b$ there is obtained a peptide mixture $M_b{}^1$ in which by means of simple reversed phase HPLC it is possible to obtain separation, usually complete separation, of the peptides $M_b{}^3$, which contain at least one chemically modified amino acid building block, from the remaining peptides $N_b{}^3$.

In addition, the peptides $M_b{}^3$, which contain at least one chemically modified amino acid building block, present in the peptide mixture $M_b{}^1$ on the one hand and the unmodified peptides $N_b{}^3$ on the other hand can each be detected at markedly different wavelengths, since the peptides $M_b{}^3$ exhibit a light absorption behaviour that is markedly different from that of the peptides $N_b{}^3$. This considerably facilitates the identification of the peptides $M_b{}^3$. Advantageously, the peptides $M_b{}^3$, as they have a colour, can be detected at wavelengths of visible light, that is to say at wavelengths between approximately 400 nm and approximately 800 nm for example in acidic solution at a wavelength of 535 nm or in alkaline solution at a wavelength of 465 nm, preferably at one of the wavelengths mentioned in Examples 10 to 15. The colourless peptides $N_b{}^3$, however, can be detected at wavelengths of ultraviolet light, for example at a wavelength of 200, 220 or 280 nm, and therefore do not interfere with the detection of the coloured peptides $M_b{}^3$.

It is also of particular interest that it is not only the peptides $M_b{}^3$ that have a colour but also the corresponding chemically modified protein $M_b$ from which the peptides $M_b{}^3$ are obtained by protease treatment. Since the chemical modification of a protein by a compound IA or a salt thereof is therefore always associated with coloration of the protein, the compounds IA and their salts can also be used as reagents for the coloration of proteins. The coloured proteins $M_b$ obtainable by reaction of the $\epsilon$-amino groups of lysine building blocks and, in isolated cases, additionally by reaction of the amino group of the N-terminal amino acid building block of corresponding colourless, unmodified proteins Nb with a compound IA or a salt thereof, can be used in a variety of ways for analytical and/or diagnostic purposes. The comments made above in connection with the separation and detection of peptides $M_b{}^3$ that have a colour also apply in analogous manner to the separation and detection of the proteins $M_b$ that have been coloured. The peptides $M_b{}^3$ can also be used for a variety of analytical and/or diagnostic purposes.

Since the investigation of proteins generally takes place in aqueous or water-containing solution, the good water-solubility of the compounds IA and their salts constitutes a further valuable property. Because the chemically modified proteins $M_b$ and the peptides $M_b{}^3$, which contain at least one chemically modified amino acid building block, are also distinguished by good water-solubility, both the reaction of proteins Nb with a compound IA or with a salt thereof and any other process steps customary in investigations of proteins which might be envisaged, for example of the kind mentioned below, can advantageously be carried out in aqueous solution, optionally with the addition of an organic solvent.

In the course of the reaction with a compound IA or with a salt thereof, the corresponding amino groups of a protein Nb of general formula $H_2N\text{-}R_x$ (Ia) wherein $R_x$ in each case is the residue of the protein, that is to say the $\epsilon$-amino groups of lysine building blocks and in isolated cases additionally the amino group of the N-terminal amino acid building block, are converted into carbamoyl or thiocarbamoyl groups, respectively, so that a chemically modified protein of formula (Ib)

wherein $R_1$, $R_2$, $R_3$, $R_4$, $R_x$ and G are as defined above and L is an oxygen or sulfur atom, is obtained. The speed of this conversion reaction increases the higher the temperature and the higher the pH value of the reaction medium. Examples of typical reaction conditions can be found in Examples 9 to 15. The stability of the carbamoyl or thiocarbamoyl bonds, respectively, in the proteins Ib is advantageously so great in normal cases that the proteins Ib can be stored for periods of several days without any appreciable decomposition taking place and that they can also withstand unimpaired the further process steps customary in investigations of proteins, such as chromatographic separations, for example by means of molecular exclusion chromatography, for example gel chromatography, or HPLC, enzymatic treatments, for example treatment with a protease, for example with trypsin or chymotrypsin, other standard reactions, for example denaturation steps, such as the reduction of disulfide bridges and the subsequent carboxymethylation of the mercapto groups, or test reactions for the analysis of the biological activity. Such process steps are known or can be carried out analogously to known process steps. Examples of details of such process steps can also be found in Examples 9 to 15. As regards the stability of the carbamoyl or thiocarbamoyl bonds in the peptides $M_b{}^3$, the comments made above for the proteins Ib apply in analogous manner.

For the above-described optimisation of the procedure for the chemical modification of proteins and for the analysis of the primary structure of such chemically modified proteins, in addition to compounds IA and their salts it is also possible to use compounds I wherein $R_1$, $R_2$, $R_3$, $R_4$ and G are as defined above, $R_5$ is hydrogen, $R_6$ is halomethyl and L is an oxygen atom, and salts thereof. These compounds are designated compounds IB below.

The comments made above for compounds IA and their salts generally apply in an analogous manner to compounds IB and their salts. However, in the chemical modification of a protein, that is to say in the reaction with that protein, the compounds IB and their salts react neither with the $\epsilon$-amino groups of lysine building blocks nor with the amino group of the N-terminal amino acid building block of that protein. On the contrary, in the course of the reaction with a compound IB or with a salt thereof specifically the mercapto groups of cysteine building blocks of a protein $N_c$ of general formula $HS\text{-}R_y$ (Id), wherein $R_y$ in each case is the residue of the protein, are converted into carbonylmethylthio groups, so that a chemically modified protein of formula (Ie)

wherein $R_1$, $R_2$, $R_3$, $R_4$, $R_y$ and G are as defined above, is obtained. Thus when compounds IB and their salts are used, generally the nature and number of the amino acid building blocks affected by a chemical modification are likewise clear and, advantageously, narrowly defined, the number of chemically modified amino acid building blocks being not greater than the number of cysteine building blocks in the protein under investigation.

The invention therefore relates also to the use of compounds I and their salts as adjuncts in the investigation of proteins, for example as reagents for the chemical modification of proteins, especially as reagents for the chemical modification of proteins that is associated with coloration. The commercial formulation of the adjuncts may also be included.

The present invention relates also to a corresponding process for the chemical modification of proteins, especially a process for the chemical modification of proteins that is associated with coloration, which process comprises reacting the proteins with a compound I or with a salt thereof.

The invention relates especially to compounds of formula I wherein $R_1$ is lower alkyl, $R_2$ is lower alkyl, $R_3$ is hydrogen, carboxy or sulfo, $R_4$ is carboxy or sulfo, G is an unsubstituted or carboxy- and/or sulfo-substituted, 1,4-phenylene group or an unsubstituted or carboxy- and/or sulfo-substituted 1,4-naphthylene group and wherein either $R_5$ and $R_6$ together are an additional bond and L is an oxygen or sulfur atom, or wherein $R_5$ is hydrogen, $R_6$ is halomethyl and L is an oxygen atom, and salts thereof.

The invention relates especially to compounds of formula I wherein $R_1$ is lower alkyl, $R_2$ is lower alkyl, $R_3$ is hydrogen, carboxy or sulfo, $R_4$ is carboxy or sulfo, G is an unsubstituted or carboxy- and/or sulfo-substituted 1,4-phenylene group or an unsubstituted or carboxy- and/or sulfo-substituted 1,4-naphthylene group, $R_5$ and $R_6$ together are an additional bond and L is an oxygen or sulfur atom, and salts thereof.

The invention relates more especially to compounds of formula I wherein $R_1$ is $C_1$-$C_4$alkyl, such as methyl or ethyl, $R_2$ is $C_1$-$C_4$alkyl, such as methyl or ethyl, $R_3$ is hydrogen or sulfo, $R_4$ is sulfo, G is an unsubstituted or sulfo-substituted 1,4-phenylene group and wherein either $R_5$ and $R_6$ together are an additional bond and L is an oxygen or sulfur atom, or wherein $R_5$ is hydrogen, $R_6$ is iodomethyl and L is an oxygen atom, and salts thereof.

The invention relates especially to compounds of formula I wherein $R_1$ is $C_1$-$C_4$alkyl, such as methyl or ethyl, $R_2$ is $C_1$-$C_4$alkyl, such as methyl or ethyl, $R_3$ is hydrogen or sulfo, $R_4$ is sulfo, G is an unsubstituted or sulfo-substituted 1,4-phenylene group, $R_5$ and $R_6$ together are an additional bond and L is an oxygen or sulfur atom, and salts thereof.

The invention relates especially to compounds of formula I wherein $R_1$ is $C_1$-$C_4$alkyl, such as methyl, $R_2$ is $C_1$-$C_4$alkyl, such as methyl, $R_3$ is hydrogen, $R_4$ is sulfo, G is an unsubstituted 1,4-phenylene group and wherein either $R_5$ and $R_6$ together are an additional bond and L is a sulfur atom, or wherein $R_5$ is hydrogen, $R_6$ is iodomethyl and L is an oxygen atom, and salts thereof.

The invention relates more especially to compounds of formula I wherein $R_1$ is $C_1$-$C_4$alkyl, such as methyl, $R_2$ is $C_1$-$C_4$alkyl, such as methyl, $R_3$ is hydrogen, $R_4$ is sulfo, G is an unsubstituted 1,4-phenylene group, $R_5$ and $R_6$ together are an additional bond and L is a sulfur atom, and salts thereof.

The invention relates specifically to the novel compounds of formula I mentioned in the Examples and their salts.

The present invention relates also to a process for the preparation of a compound I or a salt thereof, which process comprises, for example: in a compound of formula or in a salt thereof, converting the NH2 group into a group of formula and, if desired, separating a mixture of isomers obtainable in accordance with the process into the components and isolating the desired isomer I, resolving a mixture of enantiomers or diastereoisomers obtainable in accordance with the process into the individual enantiomers or diastereoisomers and isolating the desired enantiomer or diastereoisomer, and/or converting a free compound I obtainable in accordance with the process into a salt or converting a salt obtainable in accordance with the process into the free compound I or into a different salt.

The reactions described hereinbefore and hereinafter are carried out in a manner known per se, for example in the presence of a catalyst and/or in the absence or, usually, in the presence of a suitable inert solvent or diluent or a mixture thereof, the reactions being carried out, as necessary, with cooling, at room temperature or with heating, for example in a temperature range of from approximately $-80°$ C. to the boiling temperature of the reaction medium, preferably from approximately $-20°$ C. to approximately $+150°$ C., and, if necessary, in a closed vessel, under pressure, in an inert gas atmosphere and/or under anhydrous conditions.

Some of the starting materials of formulae II, IIa, III, IV, IVa and V mentioned hereinbefore and hereinafter, which are used in the preparation of compounds I or their salts, are known or they can be prepared according to methods known per se.

Starting materials having basic centres can, for example, be in the form of acid addition salts, for example with the acids mentioned above, whilst starting compounds having acidic groups can form salts with bases, for example of the kind mentioned above.

The conversion of the NH2 group in a compound II, or in a salt thereof, into a group Ic can be carried out, for example, by reacting the compound II or a salt thereof with a compound of formula wherein L is an oxygen or sulfur atom and $Z_1$ and $Z_2$ either independently of one another each represent a nucleofugal leaving group $G_1$ or together represent free or functionally modified oxo $G_2$ or wherein L is an oxygen atom, $Z_1$ is a nucleofugal leaving group $G_1$ and $Z_2$ is halomethyl.

Nucleofugal leaving groups $G_1$ are, for example, free, etherified or esterified hydroxy or mercapto groups, also amino, ammonium or sulfonium groups. Etherified hydroxy is, for example, lower alkoxy, such as methoxy or ethoxy, or unsubstituted or substituted phenyl-lower alkoxy, such as unsubstituted or substituted benzyloxy. Esterified hydroxy is especially hydroxy esterified by a mineral acid or an organic sulfonic acid, especially halogen, such as chlorine, bromine or iodine, sulfonyloxy, such as unsubstituted or halo-substituted lower alkanesulfonyloxy, for example methanesulfonyloxy or trifluoromethanesulfonyloxy, cycloalkanesulfonyloxy, for example cyclohexanesulfonyloxy, or unsubstituted or lower alkyl- or halo-substituted benzenesulfonyloxy, for example benzenesulfonyloxy, p-bromophenylsulfonyloxy or p-toluenesulfonyloxy, also lower alkanoyloxy, for example acetoxy or pivaloyloxy. Etherified mercapto is, for example, lower alkylthio, such as methylthio or ethylthio, or unsubstituted or substituted phenylthio, such as phenylthio or p-tolylthio. Esterified mercapto groups are, for example, lower alkanoylthio groups, such as acetylthio. Amino groups are, for example, amino, N-lower alkylamino, N,N-di-lower alkylamino or N-lower alkanoylamino groups, also N,N-lower alkyleneamino or N,N-aza-, N,N-oxa- or N,N-thia-lower alkyleneamino groups, for example dimethylamino or diethylamino, also pyrrolidino, piperidino, morpholino or thiomorpholino, also anilino. Ammonium groups are, for example, tertiary or quaternary ammonium groups corresponding to the amino groups mentioned above, such as tri-lower alkylammonio or pyridinio. Sulfonium groups are, for example, di-lower alkylsulfonium groups, such as dimethylsulfonium.

Free or functionally modified oxo $G_2$ is, for example, oxo, thioxo or a group $=N\text{-}R'$. Groups $=N\text{-}R'$ are, for example, those groups in which $R'$ is hydrogen, lower alkyl or an acyl radical, such as lower alkanoyl, unsubstituted or substituted benzoyl, pyridoyl or lower alkanesulfonyl, for example imino, N-lower alkylimino, N-lower alkanoylimino, unsubstituted or substituted N-benzoylimino or N-lower alkanesulfonylimino groups.

Compounds IIa preferably used for the preparation of compounds I wherein $R_5$ and $R_6$ together are an additional bond, or salts thereof, are, for example, thiophosgene ($Z_1=Z_2=$chlorine) and carbon disulfide ($Z_1$ and $Z_2=$thioxo) which result in compounds I wherein L is a sulfur atom, or salts thereof, and phosgene ($Z_1=Z_2=$chlorine) which results in compounds I wherein L is an oxygen atom, or salts thereof.

Compounds IIa preferably used for the preparation of compounds I wherein $R_5$ is hydrogen and $R_6$ is halomethyl, or salts thereof, are, for example, haloacetic acids ($Z_1=$hydroxy; $Z_2=$halomethyl; $L=$oxygen atom) and corresponding reactive haloacetic acid derivatives ($Z_1$ for example=halogen, lower alkoxy or sulfonyloxy).

The reaction of a compound II or a salt thereof with a compound IIa is carried out in customary manner, for example optionally in the presence of a condensation agent, such as a suitable base, and in the case of the reaction with compounds IIa wherein $Z_1$ and $Z_2$ together are thioxo, optionally in the presence of a sulfur-binding agent, and in the case of the reaction with compounds IIa wherein $Z_1$ is $G_1$, $Z_2$ is halomethyl and L is an oxygen atom, optionally in the presence of a water-binding agent, in the absence or, usually, in the presence of a suitable inert solvent or diluent or a mixture thereof and, as necessary, with cooling, at room temperature or with heating, for example in a temperature range of from approximately $-80°$ C. to approximately $+200°$ C., preferably from approximately $-20°$ C. to approximately $+150°$ C., and, if necessary, in a closed vessel, under pressure and/or under an inert gas, such as nitrogen.

Suitable bases are, for example, alkali metal hydroxides, hydrides, amides, alkanolates, carbonates, triphenylmethylides, di-lower alkylamides, amino-lower alkylamides and lower alkylsilylamides, or naphthaleneamines, lower alkylamines, basic heterocycles, ammonium hydroxides and carbocyclic amines. Examples that may be mentioned are sodium hydroxide, hydride, amide, ethanolate or carbonate, potassium tert.-butanolate or carbonate, lithium triphenylmethylide, lithium dissopropylamide, potassium 3-(aminopropyl)-amide or bis-(trimethylsilyl)-amide, or dimethylaminonaphthalene, di- and tri-ethylamine, pyridine, benzyltrimethylammonium hydroxide, 1,5-diazabicyclo[4.3.0]non-5-ene (DBN) and 1,5-diazabicyclo[5.4.0]undec-5-ene (DBU).

Suitable sulfur-binding agents for the reaction with compounds IIa wherein $Z_1$ and $Z_2$ together are thioxo are, for example, oxides of phosphorus, such as tetraphosphorus decaoxide, carbodiimides, such as N,N'-dicyclohexyl carbodiimide, and derivatives of carbonic acid, such as carbonic acid esters, for example halocarbonic acid lower alkyl esters, such as chlorocarbonic acid ethyl esters.

Suitable water-binding agents for the reaction with compounds IIa wherein $Z_1$ is $G_1$, $Z_2$ is halomethyl and L is an oxygen atom are, for example, oxides of phosphorus, such as tetraphosphorus decaoxide, and carbodiimides, such as N,N'-dicyclohexyl carbodiimide or N-[3-(N,N-dimethylamino)-propyl]-N'-ethyl carbodiimide and the acid addition salts thereof, for example the hydrochloride.

Inert solvents or diluents that may be mentioned are, for example, water and, also in the form of mixtures with water, cyclic ethers, unsubstituted or halogenated aromatic hydrocarbons, halogenated lower alkanes, N,N-di-lower alkyl-lower alkanoic acid amides, phosphoric acid-lower alkylamides, di-lower alkylsulfoxides, basic heterocycles and lower alkanols, such as tetrahydrofuran, dioxane, benzene, toluene, xylene, chlorobenzene, 1,2-dichlorobenzene, trichloromethane, N,N-dimethylformamide, hexamethylphosphoric acid triamide, dimethyl sulfoxide, pyridine, N-methylmorpholine, methanol and ethanol.

The starting material II or a salt thereof can be prepared analogously to known methods, for example by hydrolysis, that is to say by reaction with water, of a compound of formula (III)

wherein Y is an acyl radical, or a salt thereof.

Acyl radicals Y are, for example, acyl radicals derived from an organic carboxylic or sulfonic acid.

Acyl derived from an organic carboxylic acid is, for example, the radical of an aliphatic or monocyclic-aromatic carboxylic acid, such as lower alkanoyl or unsubstituted or substituted benzoyl, also pyridoyl.

Acyl derived from an organic sulfonic acid is, for example, lower alkanesulfonyl.

Lower alkanoyl is, for example, $C_2$-$C_5$alkanoyl, such as acetyl, propionyl, butyryl, isobutyryl or pivaloyl.

Unsubstituted or substituted benzoyl is, for example, benzoyl, p-chlorobenzoyl or p-nitrobenzoyl.

Lower alkanesulfonyl is, for example, $C_1$-$C_4$alkanesulfonyl, such as methane- or ethane-sulfonyl.

The hydrolysis of a compound III or a salt thereof is carried out in customary manner, for example in the presence of a hydrolysing agent and optionally in the absence or, usually, in the presence of a suitable inert solvent or diluent or a mixture thereof, the operation being carried out, as necessary, with cooling, at room temperature or with heating, for example in a temperature range of from approximately −80° C. to approximately +200° C., preferably from approximately −20° C. to approximately +150° C., and, if necessary, in a closed vessel, under pressure and/or under an inert gas, such as nitrogen.

Suitable hydrolysing agents are, for example, acids or bases. Suitable acids are, for example, inorganic or organic protonic acids, such as mineral acids, for example sulfuric acid or hydrohalic acids, for example hydrochloric acid, sulfonic acids, for example lower alkanesulfonic acids or unsubstituted or substituted benzenesulfonic acids, for example methane- or p-toluene-sulfonic acid, or carboxylic acids, for example lower alkanecarboxylic acids, for example acetic acid, whilst bases that can be used are, for example, those mentioned above, especially sodium or potassium hydroxide.

Suitable inert solvents or diluents are especially those mentioned above, more especially water and aqueous lower alkanols, such as aqueous methanol or ethanol.

The starting material III or a salt thereof can be prepared analogously to known methods, for example by reaction of a salt of formula wherein A is the anion of a protonic acid, with a compound of formula or with a salt thereof.

Anions A of protonic acids in salts IV are, for example, anions of the acids mentioned above for the formation of acid addition salts of compounds I, especially anions of strong inorganic protonic acids, such as anions of mineral acids, for example sulfuric acid, a phosphoric acid or a hydrohalic acid, or of tetrafluoroboric acid, or anions of strong organic carboxylic acids, such as lower alkanecarboxylic acids, for example formic acid or acetic acid, for example the sulfate, phosphate, chloride, bromide, tetrafluoroborate or acetate ion.

The reaction of a salt IV with a compound IVa or with a salt thereof is effected analogously to known procedures under the customary reaction conditions, for example in an inert solvent or diluent, for example of the kind mentioned above, preferably in water, optionally in the presence of an acidic agent, for example in the presence of one of the acids mentioned above, and/or with cooling, at room temperature or with heating, for example in a temperature range of from approximately −20° to approximately +50° C., preferably from approximately 0° to approximately +30° C.

The starting material IV is known or can be prepared analogously to known methods, for example by reaction of a compound of formula or a salt thereof, with nitrous acid, the reaction being carried out under the reaction conditions customarily used, for example in a solvent or diluent, preferably in water, and/or with cooling, at room temperature or with heating, for example in a temperature range of from approximately −20° to approximately +50° C. The nitrous acid is preferably produced in situ, for example by reaction of an alkali metal nitrite, such as sodium nitrite, with a strong protonic acid, for example a hydrohalic acid, such as hydrochloric acid, or a lower alkanecarboxylic acid, such as formic acid or glacial acetic acid.

In an especially preferred form, a compound V or a salt thereof is reacted as described above with nitrous acid, which is, for example, formed in situ, and the salt IV initially formed is then further reacted, without being isolated and/or additionally purified, in situ according to the invention with a compound IVa or with a salt thereof to form the desired compound III.

The compounds IVa and their salts are known or can be prepared analogously to known methods.

The starting material IIa is also known or can be prepared analogously to known methods.

Salts of compounds I can be produced in a manner known per se. Thus, for example, acid addition salts of compounds I are obtained by treatment with an acid or a suitable ion exchange reagent. Acidic compounds I can be converted into salts with bases, for example, by treatment with a base or with a suitable ion exchange reagent. Salts of compounds I can be converted into the free compounds I in customary manner; for example acid addition salts can be converted by treatment with a suitable basic agent, and salts with bases can be converted, for example, by treatment with a suitable acidic agent.

Depending upon the procedure and reaction conditions, the compounds I having salt-forming, especially acidic, properties may be obtained in free form or in the form of salts.

As a result of the close relationship between the novel compound I in free form and in the form of its salts, hereinbefore and hereinafter a free compound I or its salts should be understood as meaning also the corresponding salts or the free compound I, respectively, where appropriate and expedient.

The novel compounds I, including their salts, can also be obtained in the form of their hydrates or may include other solvents, for example those used for the crystallisation of compounds in solid form.

Depending upon the starting materials and procedures chosen, the novel compounds I may be in the form of one of the possible isomers or in the form of a mixture thereof. Depending upon the molecular symmetry, for example depending upon the number and the absolute and relative configuration of the chiral centres, such as asymmetric carbon atoms, as pure isomers there may be obtained, for example, pure enantiomers and/or pure diastereoisomers, such as pure cis/trans isomers or meso-compounds. Accordingly, as isomeric mixtures there may be obtained, for example, enantiomeric mixtures, such as racemates, diastereoisomeric mixtures or mixtures of racemates.

Resulting diastereoisomeric mixtures and mixtures of racemates can be separated into the pure diastereoisomers or racemates in known manner on the basis of the physico-chemical differences between the constituents, for example by fractional crystallisation.

Resulting enantiomeric mixtures, such as racemates, can be resolved into the enantiomers by known methods, for example by recrystallisation from an optically active solvent, by chromatography on chiral adsorbents, with the aid of suitable microorganisms, by cleaving with specific, immobilised enzymes, by means of the formation of inclusion compounds, for example using chiral Crown ethers, in which case only one enantiomer is complexed, or by conversion into diastereoisomeric salts, for example by reaction of a basic end product racemate with an optically active acid, such as a carboxylic acid, for example tartaric or malic acid, or a sulfonic acid, for example camphorsulfonic acid, and separation of the mixture of diastereoisomers obtained in this manner, for example on the basis of their different solubilities, into the diastereoisomers from which the desired enantiomer can be freed by the action of suitable agents. Advantageously, the more active enantiomer is isolated.

The invention also relates to those forms of the preparation process according to which a compound obtainable as intermediate at any stage of the process is used as starting material and the remaining steps are carried out, or a starting material is used in the form of a derivative or salt and/or its racemates or enantiomers or, especially, is formed under the reaction conditions.

In the preparation process of the present invention it is preferable to use those starting materials which result in the compounds I described at the beginning as being especially valuable. The invention relates also to novel starting materials which were developed specifically for the preparation of the compounds I, to their use and to processes for their preparation, the variables $R_1$, $R_2$, $R_3$, $R_4$, $R_5$, $R_6$, G and L having the meanings indicated for the groups of compounds of formula I that are preferred in each case.

In this connection, special mention should be made of compounds of formula (II)

and their salts, to which the comments made above for salts of compounds I apply in analogous manner. These can be used in an especially advantageous manner as starting materials for the preparation of compounds I or their salts, for example in accordance with the process described above.

The invention accordingly relates also to compounds of formula II wherein $R_1$ is lower alkyl, $R_2$ is lower alkyl, $R_3$ is hydrogen, carboxy or sulfo, $R_4$ is carboxy or sulfo, and G is an unsubstituted or substituted 1,4-phenylene group or an unsubstituted or substituted 1,4-naphthylene group, and salts thereof, to the use of these compounds and their salts and to a process for the preparation of these compounds and their salts.

The variables in formula II have, for example, the preferred meanings given under formula I.

The invention relates in this respect especially to compounds of formula II wherein $R_1$ is lower alkyl, $R_2$ is lower alkyl, $R_3$ is hydrogen, carboxy or sulfo, $R_4$ is carboxy or sulfo, and G is an unsubstituted or carboxy- and/or sulfo-substituted 1,4-phenylene group or an unsubstituted or carboxy- and/or sulfo-substituted 1,4-naphthylene group, and salts thereof.

The invention relates in this respect more especially to compounds of formula II wherein $R_1$ is $C_1$–$C_4$alkyl, such as methyl or ethyl, $R_2$ is $C_1$–$C_4$alkyl, such as methyl or ethyl, $R_3$ is hydrogen or sulfo, $R_4$ is sulfo, and G is an unsubstituted or sulfo-substituted 1,4-phenylene group, and salts thereof.

The invention relates in this respect more especially to compounds of formula II wherein $R_1$ is $C_1$–$C_4$alkyl, such as methyl, $R_2$ is $C_1$–$C_4$alkyl, such as methyl, $R_3$ is hydrogen, $R_4$ is sulfo, and G is an unsubstituted 1,4-phenylene group, and salts thereof.

The invention relates in this respect specifically to the novel compounds of formula II mentioned in the Examples and to their salts.

The present invention relates also to a process for the preparation of a compound II or a salt thereof, which process comprises, for example, hydrolysing a compound of formula (III)

wherein Y is an acyl radical, or a salt thereof, for example as described above, and, if desired, separating a mixture of isomers obtainable in accordance with the process into the components and isolating the desired isomer II, resolving a mixture of enantiomers or diastereoisomers obtainable in accordance with the process into the individual enantiomers or diastereoisomers and isolating the desired enantiomer or diastereoisomer, and/or converting a free compound II obtainable in accordance with the process into a salt or converting a salt obtainable in accordance with the process into the free compound II or into a different salt.

The preparation of compounds III or salts thereof is described above.

Subsequent operations which may, if desired, be carried out on compounds II or their salts obtainable in accordance with the process or by other means are especially separations of enantiomers or diastereoisomers and conversions into one another of salts and free compounds II analogous to those indicated for compounds I and these operations are also carried out in analogous manner.

The invention relates also to the use of compounds II or their salts as starting materials for the preparation of compounds I or their salts.

It is possible, to carry out the above-described optimised procedure for the chemical modification of proteins and for the analysis of the primary structure of such chemically modified proteins, that is to say the sequence consisting of the chemical modification by means of a compound I or a salt thereof, optional denaturation, protease treatment and HPLC, also automatically, using a device specifically designed for this purpose.

Figure 1:
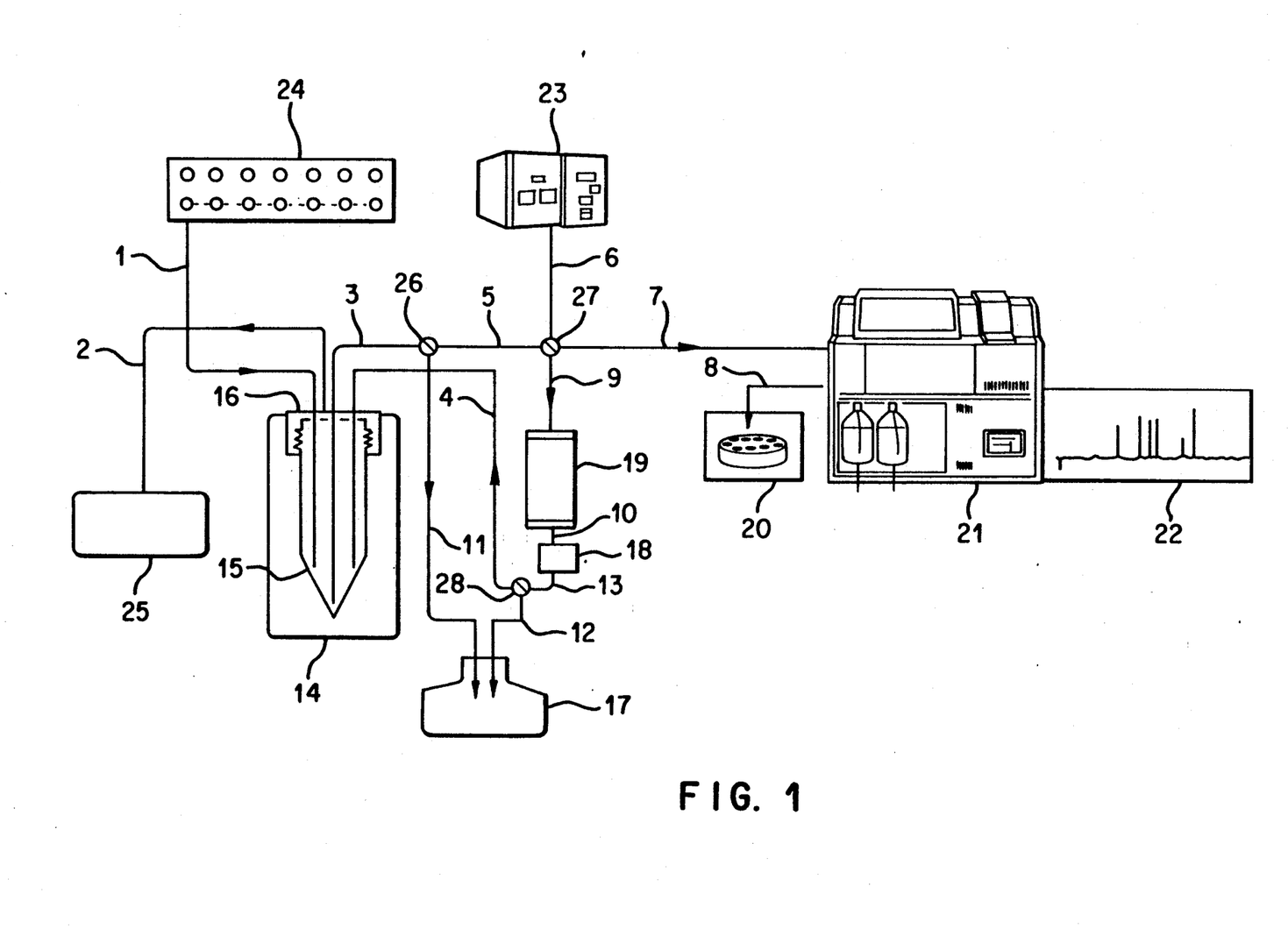

The design of this device is schematically shown in FIG. 1. The device comprises a syringe pump (24), which component (24) serves to deliver a sample of the protein which is to be chemically modified by means of a compound I or a salt thereof, solvents, reagents and/or catalysts, that are necessary for the said steps of chemical modification by means of a compound I or a salt thereof, optional denaturation and protease treatment, inert gas, and washing solution through the connection (1) into the reactor (15), which component (15) is equipped with a screw cap (16) and is installed within a heating-jacket (14), a vacuum pump (25), which component (25) enables by means of the connection (2) the evacuation of the reactor (15) for the purpose of the concentration of the contents of the reactor (15), a connection (3), which component (3), by means of a slight excess pressure of inert gas delivered from the syringe pump (24) through the connection (1), serves to deliver the contents of the reactor (15), when the chemical modification or the optional denaturation step has been carried out, through the valve (26), the connection (5), the valve (27) and the connection (9) to the desalting unit (19), or serves to deliver the contents of the reactor (15), when the protease treatment step has been carried out, through the valve (26), the connection (5), the valve (27) and the connection (7) to the HPLC component (21), to which component (21) a plotter (22) and through the connection (8) a fraction collector (20) are attached, or serves to deliver the washing solution contained in the reactor (15) through the valve (26) and the connection (11) to the waste reservoir (17), a pump (23), which component (23) delivers eluent through the connection (6), the valve (27) and the connection (9) to the desalting unit (19), a connection (10), which component (10) serves to deliver the eluate which is eluted from the desalting unit (19) to the detector (18), which component (18) serves to control the valve (28) in such a way that the eluate which is eluted from the desalting unit (19), when it contains the chemically modified protein prepared in the chemical modification step or optionally the denatured chemically modified protein prepared in the optional denaturation step is delivered through the connection (4) into the reactor (15), and when it contains no such chemically modified protein or denatured chemically modified protein is delivered through the connection (12) into the waste reservoir (17), and a connection (13), which component (13) serves to deliver the eluate from the detector (18) to the valve (28). The device according to the invention comprises the components (1) to (28).

The reactor (15) is in its size and shape comparable to a 1.5 ml Eppendorf tube. The reactor (15) can be made of any inert material, for example of glass, virtually inert plastics, such as polytetrafluoro ethylene, or high-quality stainless steel, preferably of a transparent material, for example of glass or transparent, virtually inert plastics. The steps of chemical modification, optional denaturation and protease treatment are carried out in the taper bottom part of the reactor with a total reaction volume of from approximately 100 to approximately 300 $\mu$l. The reactor can be stoppered by means of the screw cap (16), which preferably is made of the same material as the reactor (15). The connection (3) should reach as closely as possible to the bottom of the reactor, in order to enable a virtually complete emptying of the reactor (15).

The syringe pump (24) can deliver the educt (the protein which is to be chemically modified), the necessary solvents, reagents, for example the compound I or a salt thereof used in the chemical modification step, and/or catalysts, as well as inert gas and washing solution into the reactor (15). The syringe pump (24) is a commercially available apparatus, which is constructed in such a way that kind and quantity of the agent which is to be delivered into the reactor (15) can be chosen independently at any moment. By means of a valve contained in the syringe pump (24), the connection (1) leading into the reactor (15) can be stoppered at any time, for example, when the desired quantity of agent has been pumped into the reactor (15). The quantities which can be pumped in a single step into the reactor (15) can vary within a wide volume range, for example from approximately 1 $\mu$l to approximately 200 $\mu$l.

As vacuum pump (25) any commercially available pump can be used, preferably an oil pump. The desalting unit (19) serves to remove excess reagents and by-products contained in the reaction mixture resulting after the chemical modification step and the optional denaturation step. Customary chromatographic separation devices can be used as desalting unit (19), for example devices used for column chromatography, such as molecular exclusion chromatography, for example gel chromatography. The detector (18) is preferably evaluating the light absorption behavior of the molecules, for example the light absorption behaviour at wavelengths of the ultraviolet or especially of the visible light. Typical wavelengths are those given hereinbefore for the detector of the HPLC system. As heating jacket (14), waste reservoir (17), fraction collector (20), HPLC component (21), plotter (22) and pump (23) which delivers the eluent to the desalting unit (19) suitable commercially available components can be used.

The valve (26) can open on the one hand the connections (3) and (5) and at the same time stopper the connection (11). On the other hand, valve (26) can open the connections (3) and (11) and at the same time stopper the connection (5). The valve (27) can either open (5) and (9) and at the same time stopper (6) and (7), or open (5) and (7) and at the same time stopper (6) and (9), or open (6) and (9) and at the same time stopper (5) and (7). The valve (28) can either open (4) and (13) and at the same time stopper (12), or open (12) and (13) and at the same time stopper (4). Commercially available valves of suitable type can be used.

The connections (1) and (3) through (13) can be made of any inert material, for example of glass or virtually inert plastics, such as polytetrafluoroethylene, preferably of a transparent material, for example of glass or transparent, virtually inert plastics. The connection (2) is made of vacuum resistant tubing.

In detail, the reaction sequence is carried out as follows: A solution of the protein which is to be chemically modified by a compound I or a salt thereof is delivered by the syringe pump (24) through connection (1) into the reactor (15). Subsequently, a solution of the reagent (a compound I or a salt thereof) is delivered in the same way into the reactor (15). After the chemical modification is finished, a slight excess pressure of inert gas, for example argon, is built up in the reactor (15) (the inert gas is delivered from the syringe pump (24) via the connection (1)). The excess pressure causes the contents of the reactor (15) to be delivered via (3), (26), (5), (27) and (9) to the desalting unit (19). The valves (26) and (27) are adjusted accordingly. The connection (4) is stoppered by means of the valve (28). When the whole contents of the reactor (15) have been transferred to the desalting unit (19), the excess pressure is abandoned. The sample is then passed through the desalting unit (19) in order to purify it, the pump (23) being delivering the eluent via (6), (27) and (9) (the valve (27) is adjusted accordingly). By means of (10), (18), (13), (28) and (4), the purified chemically modified protein is delivered back into the reactor (15), the valve (28) being adjusted accordingly. The detector (18) serves to adjust the valve (28) in such a way, that only the fraction of the eluate containing the desired product is delivered into the reactor (15), whereas the other fractions are directly delivered via the connection (12) into the waste reservoir (17). The contents of the reactor (15) (eluate with purified chemically modified protein) are concentrated by means of the application of vacuum via the connection (2) using the vacuum pump (25). During the evacuation the connection (1) is stoppered by means of the valve contained in the syringe pump. Also, connections (3) and (5), respectively, (by means of the valve (27)) and (4) (by means of the valve (28)) are stoppered.

If a denaturation step is to be performed, then this is done in a manner analogous to that described for the chemical modification step, using the appropriate reagents and solvents. This denaturation step is then followed again by a purification step using the desalting unit (19) analogously. The resulting eluate is again delivered into the reactor (15) and concentrated.

Finally, the protease treatment step is carried out in the reactor (15) in a manner analogous to that described for the chemical modification step, again using the appropriate reagents and solvents. When the protease treatment is finished, the contents of the reactor (15) are delivered to the HPLC component (21) via (3), (26), (5), (27) and (7) (the valves (26) and (27) are adjusted accordingly) in a manner analogous to that described before (by means of a slight excess pressure of inert gas). When the HPLC has been performed, the chromatogram is obtained on the plotter (22). The fractions resulting from the HPLC can be collected by means of the fraction collector (20).

The reaction conditions (temperature, volume, reaction time, and so on) and the gradient of the HPLC are controlled by a pre-set program. Any catalysts or other adjuncts that are necessary in the described reactions can be delivered into the reactor (15) by means of the syringe pump (24) via (1).

The device is operated in such a fashion, that on the one hand the desalting unit (19) is continuously washed with eluent delivered from the pump (23), while a reaction (chemical modification, optional denaturation or protease treatment) is going on in the reactor (15), and that on the other hand the reactor (15) is cleaned with washing solution (delivered from the syringe pump (24) via (1)), while the sample (chemically modified protein or optionally denatured chemically modified protein) is being purified in the desalting unit (19). The washing solution of the desalting unit (19) is delivered into the waste reservoir (17) via (10), (18), (13), (28) and (12), and the washing solution of the reactor (15) is delivered to the waste reservoir (17) via (3), (26) and (11), in each case in a manner analogous to that described before for the transfer of the products and eluates.

The invention also relates to a device of the type described hereinbefore specifically designed to carry out automatically the sequence consisting of the chemical modification of a protein by means of a compound I or a salt thereof, the optional denaturation of the chemically modified protein, the protease treatment of the chemically modified and optionally denatured protein, and the HPLC of the peptide mixture resulting from the protease treatment step.

The invention also relates to a process for the manufacture of said device, characterised in that the components of the device described hereinbefore are combined in the way described hereinbefore to yield the desired device.

The invention also relates to a process for the automatic chemical modification of a protein and for the automatic analysis of the primary structure of the chemically modified protein consisting of the sequence described hereinbefore, which process is characterised in that the protein is processed using the device described hereinbefore.

The invention also relates to the use of the device described hereinbefore for the automatic performance of the sequence described hereinbefore and to the use of a compound I or a salt thereof as reagent in the chemical modification step performed in said device.

The invention relates also to the following Examples which illustrate the invention described above but are not intended to limit the scope thereof in any way. Temperatures are given in degrees Celsius. HPLC represents high-performance liquid chromatography. Lys represents lysine. Val represents valine.

EXAMPLE 1

25 ml of 0.24M sodium carbonate solution and 0.91 g (7.9 mmol; 0.6 ml) of thiophosgene are added to 1 g (3.1 mmol) of 4-amino-4'-(N,N-dimethylamino)-azobenzene-2-sulfonic acid. The reaction mixture is stirred for 30 minutes at 70°. After cooling to room temperature, the resulting product is filtered off by means of a fritted glass filter and thoroughly washed in succession with 1N hydrochloric acid, toluene and again with 1N hydrochloric acid. The black crystals are then dried in vacuo at room temperature, yielding 4'-(N,N-dimethylamino)-4-isothiocyanato-azobenzene-2-sulfonic acid. The product decomposes on heating and has no definite melting point; in the infra-red spectrum there is a strong band at 2110 cm$^{-1}$, produced by the asymmetric N=C=S stretch vibration.

4-amino-4'-(N,N-dimethylamino)-azobenzene-2-sulfonic acid can be obtained, for example, as follows:

0.9 g (8.5 mmol) of anhydrous sodium carbonate and 38 ml of water are added to 3.5 g (15 mmol) of 5-(N-acetylamino)-2-aminobenzenesulfonic acid. The reaction mixture is stirred until a clear solution has been obtained. This solution is then cooled to +10° by means of an ice bath.

After the addition of 1.22 g (17.7 mmol) of solid sodium nitrite the mixture is stirred for a further 2 minutes. The reaction mixture is then poured onto a mixture of 3.5 ml of concentrated hydrochloric acid and 25 g of crushed ice. Stirring is continued for a further 30 minutes at 0° and then a solution of 2.01 g (16.6 mmol; 2.1 ml) of N,N-dimethylaniline in 3 ml of glacial acetic acid is added to the reaction mixture. The temperature of the reaction mixture is allowed to rise to room temperature over a period of 3 to 4 hours. The precipitated product is filtered off and dried overnight in vacuo at room temperature, yielding 4-(N-acetylamino)-4'-(N,N-dimethylamino)-azobenzene-2-sulfonic acid in the form of black to purple crystals which decompose on heating and have no definite melting point.

2 g (5.5 mmol) of 4-(N-acetylamino)-4'-(N,N-dimethylamino)-azobenzene-2-sulfonic acid are dissolved in 8 ml of ethanol. After the addition of 4 ml of 11N sodium hydroxide solution, the mixture is stirred for 60 minutes at 90°. The mixture is then allowed to cool to room temperature and then 5 ml of 11.5N hydrochloric acid are added. The reaction mixture is then left overnight at +4°. The precipitated product is filtered off and washed thoroughly with 1N hydrochloric acid. After drying in vacuo at room temperature, 4-amino-4'-(N,N-dimethylamino)-azobenzene-2-sulfonic acid is obtained in the form of black to purple crystals which decompose on heating and have no definite melting point.

EXAMPLE 2

0.67 g (2.1 mmol) of 4-amino-4'-(N,N-dimethylamino)-azobenzene-2-sulfonic acid (Example 1) are dissolved in 5 ml of absolute pyridine. This solution is then added dropwise, with stirring and while cooling with ice/sodium chloride, to a mixture of 424 mg (2.1 mmol) of N,N'-dicyclohexyl carbodiimide, 5 ml of anhydrous pyridine and 1.26 g (16.6 mmol; 1 ml) of carbon disulfide. The reaction mixture is then stirred for 3 to 4 hours with the cooling being maintained. The mixture is then left to stand at room temperature for 17 hours. The pyridine and excess carbon disulfide are then removed as completely as possible under reduced pressure. Column chromatography of the residue on silica gel (150 to 200 mesh) with benzene as eluant yields 4'-(N,N-dimethylamino)-4-isothiocyanato-azobenzene-2-sulfonic acid which crystallises out when the eluate is concentrated by evaporation.

EXAMPLE 3

0.67 g (2.1 mmol) of 4-amino-4'-(N,N-dimethylamino)-azobenzene-2-sulfonic acid (Example 1) are dissolved in 5 ml of absolute pyridine. With stirring and while cooling with ice, 1.26 g (16.6 mmol; 1 ml) of carbon disulfide and 0.22 g (2.2 mmol; 0.3 ml) of triethylamine are added to the solution. The reaction mixture is then stirred for 3 to 4 hours with the cooling being maintained. The mixture is then left to stand for 17 hours at room temperature and is then concentrated to dryness by evaporation. The triethylammonium dithiocarbamate remaining behind as residue is dried overnight in vacuo and is then dissolved in 12 ml of trichloromethane. While cooling with ice, 0.22 g (2.2 mmol; 0.3 ml) of triethylamine is added to the solution. To this mixture there is then added dropwise, within a period of 4 minutes, 0.34 g (3.1 mmol; 0.3 ml) of chlorocarbonic acid ethyl ester, with stirring and while cooling with ice. The reaction mixture is left to stand for 3 to 4 hours with the cooling being maintained and is then concentrated to dryness by evaporation under reduced pressure. The crude product remaining behind as residue is purified by column chromatography as described in Example 2, yielding 4'-(N,N-dimethylamino)-4-isothiocyanato-azobenzene-2-sulfonic acid.

EXAMPLE 4

In a manner analogous to that described in Examples 1 to 3, starting from 4-amino-4'-(N,N-dimethylamino)-azobenzene-2,6-disulfonic acid and 4-(N,N-dimethylamino)-naphthalene-1-azo-(4'-aminobenzene-2'-sulfonic acid), it is also possible to obtain 4'-(N,N-dimethylamino)-4-isothiocyanato-azobenzene-2,6-disulfonic acid and 4-(N,N-dimethylamino)-naphthalene-1-azo-(4'-isothiocyanatobenzene-2'-sulfonic acid), respectively.

The starting materials can each be obtained in a manner analogous to that described in Example 1, starting from 4-(N-acetylamino)-4'-(N,N-dimethylamino)-azobenzene-2,6-disulfonic acid and 4-(N,N-dimethylamino)-naphthalene-1-azo-[4'-(N-acetylamino)-benzene-2'-sulfonic acid], respectively.

EXAMPLE 5

20 ml of chlorobenzene are cooled to 0° by cooling with ice/sodium chloride. 1.1 g (11.1 mmol) of phosgene are introduced by condensation into the cooled chlorobenzene with the customary precautions being observed. With the cooling being maintained and with vigorous stirring, a solution of 1.79 g (5.6 mmol) of 4-amino-4'-(N,N-dimethylamino)-azobenzene-2-sulfonic acid (Example 1) in 30 ml of chlorobenzene is added dropwise at such a rate that the temperature of the reaction mixture does not exceed +25°. When the dropwise addition is complete, the cooling bath is replaced by a heating bath by means of which the reaction mixture is heated to 130° within a period of 90 minutes while constant stirring is continued. In the course of this process, as soon as the reaction mixture has reached a temperature of 75°, further phosgene is slowly introduced until a clear solution is obtained. The reaction mixture is then heated under reflux, with nitrogen being passed through the mixture, until phosgene can no longer be detected in the outgoing stream of gas (about 2 hours). After cooling to room temperature, the reaction mixture is concentrated as completely as possible under reduced pressure. Column chromatography of the residue on silica gel (150 to 200 mesh) with benzene as eluant yields 4'-(N,N-dimethylamino)-4-isocyanato-azobenzene-2-sulfonic acid which crystallises out when the eluate is concentrated by evaporation.

EXAMPLE 6

In a manner analogous to that described in Example 5, starting from 4-amino-4'-(N,N-dimethylamino)-azobenzene-2,6-disulfonic acid and 4-(N,N-dimethylamino)-naphthalene-1-azo-(4'-aminobenzene-2'-sulfonic acid) it is also possible to obtain 4'-(N,N-dimethylamino)-4-isocyanato-azobenzene-2,6-disulfonic acid and 4-(N,N-dimethylamino)-naphthalene-1-azo-(4'-isocyanatobenzene-2'-sulfonic acid), respectively.

The starting materials can each be obtained in a manner analogous to that described in Example 4.

EXAMPLE 7

1.8 g (9.7 mmol) of iodoacetic acid and 1.2 g (6.3 mmol) of N-[3-(N,N-dimethylamino)-propyl]-N'-ethylcarbodiimide hydrochloride are dissolved in 9 ml of water. This solution is immediately mixed, with stirring, with a solution of 0.5 g (1.6 mmol) of 4-amino-4'-(N,N-dimethylamino)-azobenzene-2-sulfonic acid (Example 1) in 7.6 ml of a buffer solution which has a pH of 9 and consists of 50 mM sodium hydrogen carbonate solution and 50 mM sodium carbonate solution. 0.4 ml of 11N sodium hydroxide solution is then added dropwise to the mixture which is then stirred for 10 minutes at room temperature. 1N hydrochloric acid is then added dropwise until the mixture turns purple. The product that precipitates is filtered off, washed thoroughly with 100 ml of 0.1N hydrochloric acid and dried in vacuo. The dried crude product is dissolved in a mixture of 16 ml of N,N-dimethylformamide and 0.4 ml of triethylamine. Further precipitation with 1N hydrochloric acid in the manner described above, filtration and drying of the filter contents in vacuo yield the desired pure 4'-(N,N-dimethylamino)-4-(N-iodoacetyl)-amino-azobenzene-2-sulfonic acid which decomposes on heating and has no definite melting point.

EXAMPLE 8

In a manner analogous to that described in Example 7, starting from 4-amino-4'-(N,N-dimethylamino)-azobenzene-2,6-disulfonic acid and 4-(N,N-dimethylamino)-naphthalene-1-azo-(4'-aminobenzene-2'-sulfonic acid), it is also possible to obtain 4'-(N,N-dimethylamino)-4-(N-iodoacetyl)-amino-azobenzene-2,6-disulfonic acid and 4-(N,N-dimethylamino)-naphthalene-1-azo-[4'-(N-iodoacetyl)-aminobenzen-2'-sulfonic acid], respectively.

The starting materials can each be obtained in a manner analogous to that described in Example 4.

EXAMPLE 9

Monoclonal antibodies that act specifically against eglin C are chemically modified at room temperature over a period of 18 hours in a 50 mM sodium hydrogen carbonate solution by the action of a 2 mM solution of 4'-(N,N-dimethylamino)-4-isothiocyanato-azobenzene-2-sulfonic acid. Subsequent structural analysis shows that each antibody molecule has been chemically modified by 30 molecules of 4'-(N,N-dimethylamino)-4-isothiocyanato-azobenzene-2-sulfonic acid. With this degree of modification, the antibodies exhibit specificity against and affinity for recombinant eglin C that is unchanged in comparison with the unmodified antibodies. These chemically modified antibodies which have also been coloured at the same time can be used to demonstrate the presence of eglin C with the aid of the sandwich dot assay. In that assay concentrations of 1 µg/ml and above can be detected with the naked eye.

EXAMPLE 10

Hirudin, a specific inhibitor of thrombin, is chemically modified at 37° over a period of 7 hours in a 50 mM sodium hydrogen carbonate solution by the action of a 2 mM solution of 4'-(N,N-dimethylamino)-4-isothiocyanato-azobenzene-2-sulfonic acid. The hirudin so modified is subjected to gel chromatography on a Sephadex G 25 column. In the modification of the inhibitor, 1.96 mol of 4'-(N,N-dimethylamino)-4-isothiocyanato-azobenzene-2-sulfonic acid are reacted per mol of hirudin. The structure of the modified inhibitor and its biological activity are analysed and the following findings are obtained:

a) The chemically modified hirudin has a reduced inhibitor activity against thrombin, as can be seen from the fact that the corresponding dissociation constant $K_i$ is 300 times greater.

b) Monoclonal antibodies against native hirudin act also against the chemically modified hirudin.

c) The chemically modified hirudin is carboxymethylated and treated with protease V8. The resulting peptides are subjected to HPLC. At a wavelength of 536 nm two peptides are detected. Structural analysis shows that these two coloured peptides correspond to amino acid building blocks 1 to 7 and 18 to 37 and that selectively the building blocks Val-1 and Lys-27 are modified by 4'-(N,N-dimethylamino)-4-isothiocyantato0-azo-benzene-2-suflonic acid.

EXAMPLE 11

Human antithrombin is chemically modified at room temperature over a period of 15 minutes in a 50 mM sodium hydrogen carbonate solution by the action of a 1 mM solution of 4'-(N,N-dimethylamino)-4-isothiocyanato-azobenzene-2-sulfonic acid. The antithrombin so modified is subjected to gel chromatography on a Sephadex G 25 column. The structure of the modified antithrombin and its biological activity are analysed and the following findings are obtained:

a) The chemically modified antithrombin retains only 25% of its heparin cofactor activity, but its inhibitor activity against thrombin in the absence of heparin (progressive inhibitor activity) is virtually unchanged.

b) The chemically modified antithrombin is carboxymethylated and treated with trypsin. The resulting peptides are subjected to HPLC. At a wavelength of 436 nm three peptides are detected. Structural analysis shows that these three coloured peptides correspond to amino acid building blocks 91 to 111, 115 to 129 and 133 to 139 and that selectively the building blocks Lys-107, Lys-125 and Lys-136 are modified by 4'-(N,N-dimethylamino)-4-isothiocyanato-azobenzene-2-sulfonic acid.

c) If antithrombin is incubated with heparin before being acted upon by 4'-(N,N-dimethylamino)-4-isothiocyanato-azobenzene-2-sulfonic acid, the chemical modification of the building blocks Lys-107, Lys-125 and Lys-136 is inhibited by 98%, 88% and 93%, respectively.

d) The building blocks Lys-107, Lys-125 and Lys-136 of human antithrombin are accordingly of particular importance to the bonding of heparin.

EXAMPLE 12

In a manner analogous to that described in Examples 9 to 11 it is also possible to use a different compound of formula I or a salt of a compound of formula I, for example according to Examples 1 to 8, for the chemical modification of a protein.

EXAMPLE 13

The investigation of the heparin binding site of human antithrombin by means of a device of the type shown in FIG. 1 can be carried out as follows:

a) Human antithrombin (432 amino acids) and the heparin-antithrombin complex are processed one after another, the folowing steps b) through g) being carried out in each case. The device used in these steps comprises the components shown shcematically in FIG 1. The reactor (15) is made of glass. The detector (18) works on the basis of the absorption of light of a wavelength of 436 nm. The connections (1) and (3) through (13) are made of glass. The connection (2) is made of vacuum resistant tubing. An oil pump is used as vacuum pump (25). The desalting unit (19) consists of a Sephadex G 25 column.

b) Chemical modification step

Solvent: 50 mM sodium hydrogencarbonate solution (pH=8.3);

Sample 1: antithrombin, 250 µg;

Sample 2: heparin-antithrombin complex (2:1 parts by weight), 750 µg (250 µg of antithrombin and 500 µg of heparin);

Reagent of the formula I for the chemical modification: 1 mM solution of 4'-(N,N-dimethylamino)-4-isothiocyanato-azobenzene-2-sulfonic acid in the solvent mentioned;
Reaction volume: 200 μl;
Reaction temperature: +25°;
Reaction time: 7.5 minutes.

c) Desalting step
Column: Sephadex G 25 (length: 3.5 cm; internal diameter: 1 cm);
Eluent: 50 mM ammonium hydrogen carbonate solution (pH=8.0).

d) Denaturation step
Solvent: 0.5M α,α,α-tris(hydroxymethyl)methylaminehydrochloride ("tris hydrochloride") solution (pH=8.4) and 5M guanidine hydrochloride solution;
Reaction volume: 200 μl;
Reduction reagent: threo-1,4-dimercapto-2,3-butanediol (dithiothreitol, DTT), 1 mg;
Reduction temperature: +37°;
Reduction time: 2 hours;
Carboxymethylation reagent: iodoacetic acid, 2 mg;
Carboxymethylation temperature: +37°;
Carboxymethylation time: 15 minutes.

e) Desalting step
Column: Sephadex G 25 (length: 3.5 cm; internal diameter: 1 cm);
Eluent: 50 mM ammonium hydrogen carbonate solution (pH=8.0).

f) Protease treatment step
Protease: trypsin, 10 μg;
Solvent: 50 mM ammonium hydrogen carbonate solution (pH=8.0).
Reaction volume: 100 μl;
Reaction temperature: +37°;
Reaction time: 2 hours.

g) HPLC step
Column: Vydac C-18 for peptides and proteins;
Column temperature: +25°;
Solvent A: 17.5 mM sodium acetate (pH=5.0);
Solvent B: acetonitrile;
Gradient: linear from 10% B to 70% B within 30 minutes;
Flow rate: 1 ml per minute;
Detector: absorption of light of a wavelength of 436 nm.

h) The comparison of the peak patterns in the two chromatograms resulting from sample 1 and sample 2, respectively, and the sequence analysis of the coloured peptides which correspond to peaks that appear only in the chromatogram of sample 1 reveal, that the amino acid building blocks Lys-107, Lys-125 and Lys-136 are situated within the heparin binding site of human antithrombin.

EXAMPLE 14

In a manner analogous to that described in Example 13, the investigation of the hirudin binding site of human thrombin can be carried out using the device described in Example 13. Human thrombin (sample 1; 250 μg) and the hirudin-thrombin complex [sample 2; 750 μg; molar ratio (hirudin:thrombin)=(1,2:1)] are processed one after another, steps b) through g) of Example 13 being carried out analogously in each case. The comparison of the peak patterns in the two chromatograms resulting from sample 1 and sample 2, respectively, and the sequence analysis of the coloured peptides which correspond to peaks that appear only in the chromatogram of sample 1 reveal, that the amino acid building blocks Lys-21, Lys-52, Lys-65, Lys-106, Lys-107 and Lys-154 are situated within the hirudin binding site of human thrombin.

EXAMPLE 15

In a manner analogous to that described in Examples 13 and 14 it is also possible to use a different compound of formula I or a salt of a compound of formula I, for example according to Examples 1 to 8, as reagent for the chemical modification in step b) of the processing sequence carried out in the device described in Example 13.

What is claimed is:
1. A compound of the formula wherein
R$_1$ is lower alkyl;
R$_2$ is lower alkyl;
R$_3$ is hydrogen, carboxy, or sulfo;
R$_4$ is sulfo;
G is a 1,4-phenylene group which is unsubstituted or is substituted by 1–4 substituents selected from carboxy and sulfo or G is a 1,4-naphthylene group which is unsubstituted or substituted by 1–6 substituents selected from carboxy and sulfo;
R$_5$ and R$_6$ together are an additional bond; and
L is an oxygen atom or a sulfur atom; or a salt thereof; wherein lower is 1–7 carbon atoms.

2. The compound of claim 1 wherein said 1,4-phenylene group is unsubstituted or substituted by 1 or 2 substituents selected from carboxy and sulfo and said 1,4-naphthylene group is unsubstituted or substituted by 1 to 3 substituents selected from carboxy and sulfo, or a salt thereof.

3. A compound of formula I according to claim 1 wherein R$_1$ is C$_1$–C$_4$alkyl, R$_2$ is C$_1$–C$_4$alkyl, R$_3$ is hydrogen, R$_4$ is sulfo, G is an unsubstituted 1,4-phenylene group, R$_5$ and R$_6$ together are an additional bond and L is a sulfur atom, or a salt thereof.

4. 4'-(N,N-dimethylamino)-4-isothiocyanato-azobenzene-2-sulfonic acid or a salt thereof according to claim 1.

* * * * *